(12) United States Patent
Boulais et al.

(10) Patent No.: US 7,951,392 B2
(45) Date of Patent: May 31, 2011

(54) MICROARRAY DRUG DELIVERY COATINGS

(75) Inventors: Dennis R. Boulais, Danielson, CT (US);
Maria Palasis, Wellesley, MA (US);
Samuel Epstein, Newton, MA (US);
Wendy Naimark, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1533 days.

(21) Appl. No.: 10/219,668

(22) Filed: Aug. 16, 2002

(65) Prior Publication Data

US 2004/0034337 A1 Feb. 19, 2004

(51) Int. Cl.
*A61F 2/00* (2006.01)

(52) U.S. Cl. ......... 424/425; 424/422; 424/424; 424/426

(58) Field of Classification Search .................. 424/485, 424/422–428, 448, 449, 482, 475, 450; 604/265, 604/53
See application file for complete search history.

(56) References Cited

U.S. PATENT DOCUMENTS

| | | | |
|---|---|---|---|
| 5,304,121 A | 4/1994 | Sahatjian | |
| 5,443,458 A | 8/1995 | Eury | |
| 5,447,724 A * | 9/1995 | Helmus et al. | 424/426 |
| 5,824,049 A * | 10/1998 | Ragheb et al. | 623/1.44 |
| 5,873,904 A * | 2/1999 | Ragheb et al. | 623/1.13 |
| 5,948,018 A * | 9/1999 | Dereume et al. | 623/1.12 |
| 5,972,027 A | 10/1999 | Johnson | |
| 5,997,517 A * | 12/1999 | Whitbourne | 604/265 |
| 6,120,536 A | 9/2000 | Ding et al. | |
| 6,210,703 B1 | 4/2001 | Novich | |
| 6,299,604 B1 * | 10/2001 | Ragheb et al. | 604/265 |
| 6,299,905 B1 | 10/2001 | Peterson et al. | |
| 6,339,130 B1 | 1/2002 | Bennett et al. | |
| 6,368,658 B1 | 4/2002 | Schwarz et al. | |
| 6,371,979 B1 | 4/2002 | Beyar et al. | |
| 6,395,326 B1 | 5/2002 | Castro et al. | |
| 6,468,819 B1 | 10/2002 | Kim et al. | |
| 6,805,809 B2 | 10/2004 | Nuzzo et al. | |
| 6,849,089 B2 | 2/2005 | Stoll | |
| 2001/0027340 A1 | 10/2001 | Wright et al. | |
| 2003/0068355 A1 | 4/2003 | Shanley et al. | |
| 2003/0149479 A1 | 8/2003 | Snyder et al. | |
| 2004/0127976 A1 | 7/2004 | Diaz | |
| 2004/0254635 A1 | 12/2004 | Shanley et al. | |

FOREIGN PATENT DOCUMENTS

| | | |
|---|---|---|
| EP | 0 604 022 A1 | 6/1994 |
| EP | 0 734 721 A2 | 10/1996 |
| WO | WO 9632907 A1 * | 10/1996 |
| WO | WO 01/15751 A1 | 3/2001 |
| WO | WO 03/030879 A1 | 4/2003 |
| WO | WO 2004/016298 A1 | 2/2004 |
| WO | WO 2004/087251 A1 | 10/2004 |

* cited by examiner

*Primary Examiner* — Michael G Hartley
*Assistant Examiner* — Micah-Paul Young
(74) *Attorney, Agent, or Firm* — Kenyon & Kenyon LLP

(57) ABSTRACT

The present invention relates to microarray polymeric barriers designed to control the release rate of therapeutic agents. By varying the thickness of the coating or affecting, physically and/or chemically, the constituents of the barrier composition, the release profile of the underlying therapeutic agent can be modified and controlled.

20 Claims, 4 Drawing Sheets

MICROARRAY DRUG DELIVERY COATINGS

TECHNICAL FIELD

The present invention relates to the controlled delivery of therapeutic agents to a target site of an organic vessel.

BACKGROUND

The systematic administration of drug agents, such as by transoral or intravenous means, treats the body as a whole even though the disease to be treated may be localized. When a disease to be treated is localized, a localized delivery of the drug agent is often the more advantageous approach. Moreover, certain invasive treatments require the insertion and expansion of stent devices in blood vessels, urinary tracts or other locations difficult to otherwise access. Conventionally, such stents are delivered to a location of interest utilizing a vascular catheter, or similar transluminal device. The stents may be medically-coated for localized delivery of one or more therapeutic agents.

U.S. Pat. No. 6,120,536, incorporated herein by reference for background information, discloses a type of self-expanding stent having a flexible tubular body formed of several individual flexible thread elements each of which extends in a helix configuration with the centerline of the body serving as a common axis. The treated elements are wound in the same direction but are displaced axially relative to each other and meet, under crossing, a like number of elements also so axially displaced, but having the opposite direction of winding. This configuration provides a resilient braided tubular structure which assumes stable dimensions upon relaxation. Axial tension produces elongation and corresponding diameter contraction that allows the stent to be mounted on a catheter device and conveyed through the vascular system as a narrow elongated device. Once tension is relaxed in situ, the device at least substantially reverts to its original shape.

Implanted stents have been used to carry medicinal agents, such as thrombolytic agents. For example, U.S. Pat. No. 5,163,952 to Froix discloses a thermal memoried expanding plastic stent device formulated to carry a medicinal agent in the material of the stent itself. Pinchuk, in U.S. Pat. No. 5,092,877, discloses a stent of a polymeric material which may have a coating associated with the delivery of drugs. Other implantable devices can include bio-active agents such as therapeutic and medicinal compositions designed to combat a particular ailment. Stents can also include a DNA coating for gene therapy to serve diverse medical purposes, including slowing down growth of certain cells. Genes are usually delivered into the patient's cells through a vector, such as a retro virus having genetically engineered DNA to include a desired DNA sequence. In the context of angioplasty, incorporation of appropriate DNA into the coronary artery walls near the treatment site can be beneficial to inhibit restenosis.

Thus, stents and other similar implants have been used as the delivery vehicle for the DNA or therapeutic agent. The stent provides the additional advantage of resisting artery reclosure by recoil after the expansion of the vessel wall. In this application, it is desirable to have the plasmid DNA or therapeutic agent released and expressed over a predetermined period of time in the target area.

In some cases, the delivery of DNA or therapeutic agent can be inefficient, requiring large amounts of DNA and long delivery times for the stent to be an effective delivery system. This in turn can require large amounts of polymer coating on the stent, adapted to hold and release the DNA over the required period of time. However, if the coating is too thick, expansion of the stent can cause cracking of the coating, thus reducing the effectiveness of the coating. In addition, excessive coating may also cover the windows formed in the stent between the wires forming the stent, which normally allow passage of oxygen into the walls of the artery. On the other hand, if the coating is too thin, the entire supply of DNA or the therapeutic agent can be released within a short frame of time.

Thus, controlled drug delivery from medical device coatings remains difficult to control and fine tune. As described, the conventional technologies rely on bulk phase release of therapeutic agents from carrier coatings. In this manner, often a rapid burst of the therapeutic agent occurs. Thus far the modification of release profile has been restricted to formulation chemistry changes. This strategy that has proven ineffective in controlling the drug release profile.

SUMMARY OF THE INVENTION

The invention is directed to controlling the release rate of therapeutic agent into the body by providing a microarray-type placement of polymeric barriers over the sites where therapeutic agents have been deposited.

In certain embodiments, the invention relates to a medical device for controlled delivery of a therapeutic agent to a desired location within a body. The medical device includes a bio-compatible substrate having a therapeutic agent deposited on a plurality of sites thereon. A bio-absorbable barrier composition can be coated over each of the therapeutic sites. As will be described in greater detail below, in certain embodiments, the bio-absorbable barrier can be a porous, a non-porous and/or a dissolvable bio-stable polymer. The coating thickness of the barrier layer can be controlled such that each site can have a different thickness, thereby providing a different rate of release for the therapeutic agent.

Non-limiting examples of biodegradable polymers include poly-tyrosine polymers, PEG, PLGA, PLGA/PLA/PGA (polyesters) and polyorthoethers. Non-limiting examples of dissolvable bio-compatible material include collagen, heparin, dextran, poloxamer, and hyaluronic acid. Bio-stable material can be made porous with treatment with super critical $CO_2$ or addition of certain excipients such as, polyethylene glycol (PEG), poloxamer, dextran or albumin.

In further embodiments, the invention relates to a bio-compatible substrate such as a stent, wherein one or more layer of therapeutic agent is interposed between the stent and a microarray bio-absorbable barrier. The release rate of the therapeutic agent can be controlled by controlling the thickness of the barrier which, can vary throughout the coating. In yet other embodiments of the invention, a biodegradable barrier, or a combination of several different biodegradable/bio-absorbable barriers, can form a microarray designed to predictably control the release rate of the therapeutic agent. In other embodiments, the invention includes bio-stable membrane that allows dry release which is controlled by the membrane's pore or permeability.

In yet another embodiments of the invention, the bio-compatible substrate is coated with a plurality of therapeutic agents some having an immediate release effect and some having a more sustained release. Thus, one or more therapeutic agents can be deposited at a first site of the substrate and can be made available for a quick release. On the other hand, one or more therapeutic agents can be deposited at an alternate site and can be adapted for a later release or for a more sustained release. Thus, in one embodiment, the invention can release many drugs at different rates or, in yet another embodiment, the invention can release on drug at different rates. According to this embodiment, a series of treatments can be administered with one implant device.

In yet further embodiments, a bio-compatible substrate can be adapted to receive one or more therapeutic agent at different sites of the substrate. The sites of the therapeutic agents and the stents can have a barrier coating of constant thickness which comprises different biodegradable, bio-stable or bio-absorbable material at different sites. According to these embodiments, each site can provide for a different release profile.

In still further embodiments, the invention provides for a method of preparing a biocompatible stent having an extended release profile. The method includes providing a substrate adapted for insertion into a body, depositing therapeutic agents at a plurality of sites on the substrate, at least partially coating each of the plurality of sites with a barrier layer having a thickness, and controlling the release rate of the therapeutic agent into the body by controlling the thickness of the barrier layer coated on each of the sites.

BRIEF DESCRIPTION OF THE DRAWINGS

These and other embodiments of the invention will be better understood with reference to the following drawings, where.

DETAILED DESCRIPTION

Figure 1:
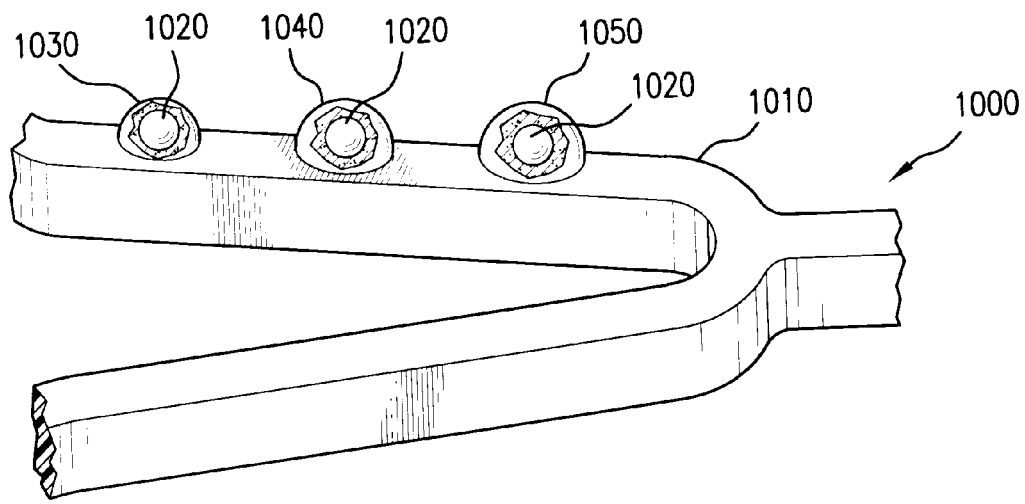
FIG. 1 is an enlarged view of one embodiment of the invention.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), virus (such as adenovirus, adenoassociated virus, retrovirus, lentivirus and .alpha.-virus), polymers, hyaluronic acid, proteins, cells and the like, with or without targeting sequences. The polymer can be a bio-stable polymer containing one or more pores. The polymer can also be a non-porous bio-stable polymer network. Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

As used herein, medical devices can include catheters, guide wires, balloons, filters (e.g. vena cava filters), stents, stent grafts, vascular grafts, intraluminal paving systems or other known bio-compatible implants. Catheters can include, among others, infusion catheters and direct injection catheters. As used herein the term substrate refers to the substrate used in any of the above non-limiting medical devices. The medical devices are conventionally placed, among others, in coronary vasculature, esophagus, trachea, colon, bladder, heart, vessels, lumens, intestines, biliary tract, urinary tract, prostate and brain.

FIG. 1 is an enlarged view of one embodiment of the invention. Referring to FIG. 1, an enlarged segment 1010 of stent 1000 is shown to have deposited thereon therapeutic agents 1020 in three different sites. As can be seen in FIG. 1, the segments 1010 of the stent leave open areas between the segments, forming an open lattice structure as is well-known in the art. The therapeutic agent can be any of the known DNA or medicinal agent. As shown in the embodiment of FIG. 1, barrier layers 1030, 1040 and 1050 are coated on the therapeutic agent 1020. Barrier layer 1040 is of medium thickness when compared with the relatively thin layer 1030, or the relatively thick barrier layer 1050. Hence, by controlling the thickness of each of the various barrier layers, the release profile of the implantable medical device can be controlled to suit the desired treatment. Inasmuch as the release rate of the therapeutic agent will be a function of, among others, the barrier layer's thickness, rate of degradation or absorption of the barrier layer and mass transport rate of the therapeutic agent through the barrier layer, the release profile can be predictably devised.

In another embodiment of the invention, the therapeutic agents can be of the same or different material. More specifically, each of deposit sites 1020 can have a different therapeutic agent or different amounts of the same agent deposited therein. Moreover, sites 1020 can contain a combination of more than one therapeutic agent. Finally, sites 1020 can be deposited on the stent or embedded therein in order to accommodate the desired application.

Further in reference to FIG. 1, the barrier layers 1030, 1040 and 1050 can be arranged as microarray polymeric barriers. The topology of the array may vary depending on the desired outcome. For example, for a given therapy there may be a need for subsequent follow-up therapies in which case the material may be layered. In one embodiment, a plurality of wells can be formed on the surface with the desired drug (or drugs) deposited in each well; the surface of the wells can be covered with one or more barrier layers having the same or different constituents. On the other hand, for concurrent therapies, the array would feature material laid side-by-side so as to provide simultaneous release thereof. By creating the microarray polymeric barriers the release rate of therapeutic agents can be varied over the coating landscape. This arrangement can also prevent the so-called "Candy Wrapper" effect seen after drug/radiation stent therapy. The so-called candy wrapper effect relates to the coating at the end(s) of the stent.

Although the embodiment of FIG. 1 shows therapeutic agents 1020 and barrier layers 1030, 1040 and 1050 separately, it will be noted that the principles of the invention can be applied to a composition where the barrier layer is combined with the therapeutic agent. In this embodiment, each coating site can receive a different amount of the therapeutic agent/barrier solution.

Figure 2:
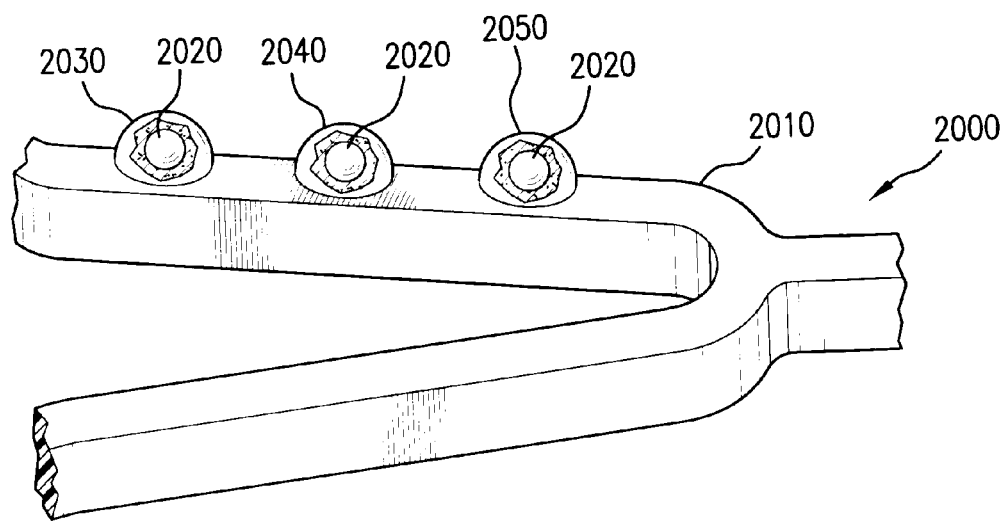
FIG. 2 is an enlarged view of another embodiment of the invention.

FIG. 2 is an enlarged view of another embodiment of the invention. Referring to the embodiment of FIG. 2, stent 2000 comprises DNA and/or therapeutic sites 2020 deposited along stent segment 2010. Barrier layers 2030, 2040 and 2050 can be arranged over segment 2010 to control the release rate of the therapeutic agent 2010. In the embodiment of FIG. 2, the microarrays of barrier layers 2030, 2040 and 2050 have substantially the same thickness. Notwithstanding, each of the barrier layers 2030, 2040 and 2050 can comprise a different chemical composition. Inasmuch as different bio-absorbable or biodegradable materials have a different absorption/degradation rate, the release of each of sites 2030, 2040 and 2050 can be designed in advance and controlled to suit a particular treatment. It has been found that in some embodiments of the invention, the release rate is proportional to the concentration of the excipient.

Further, the embodiment of FIG. 2 can contain different therapeutic agents in each of the three sites identified as 2010. In this embodiment, for example, administration of two or more drugs can be controlled to be simultaneous or sequential. Hence, the release rate or the release profile of the medical device can be designed in advanced to complement a treatment strategy or the patient's particular conditions. That is, if barrier layer 2040 is selected to dissolve first, followed by dissolution or degradation of barrier layers 2030 and 2050 sequentially, therapeutic agents 2020 will be uncovered according to dissolution/degradation of each of 2030, 2040 and 2050 barrier layers.

Figure 3:
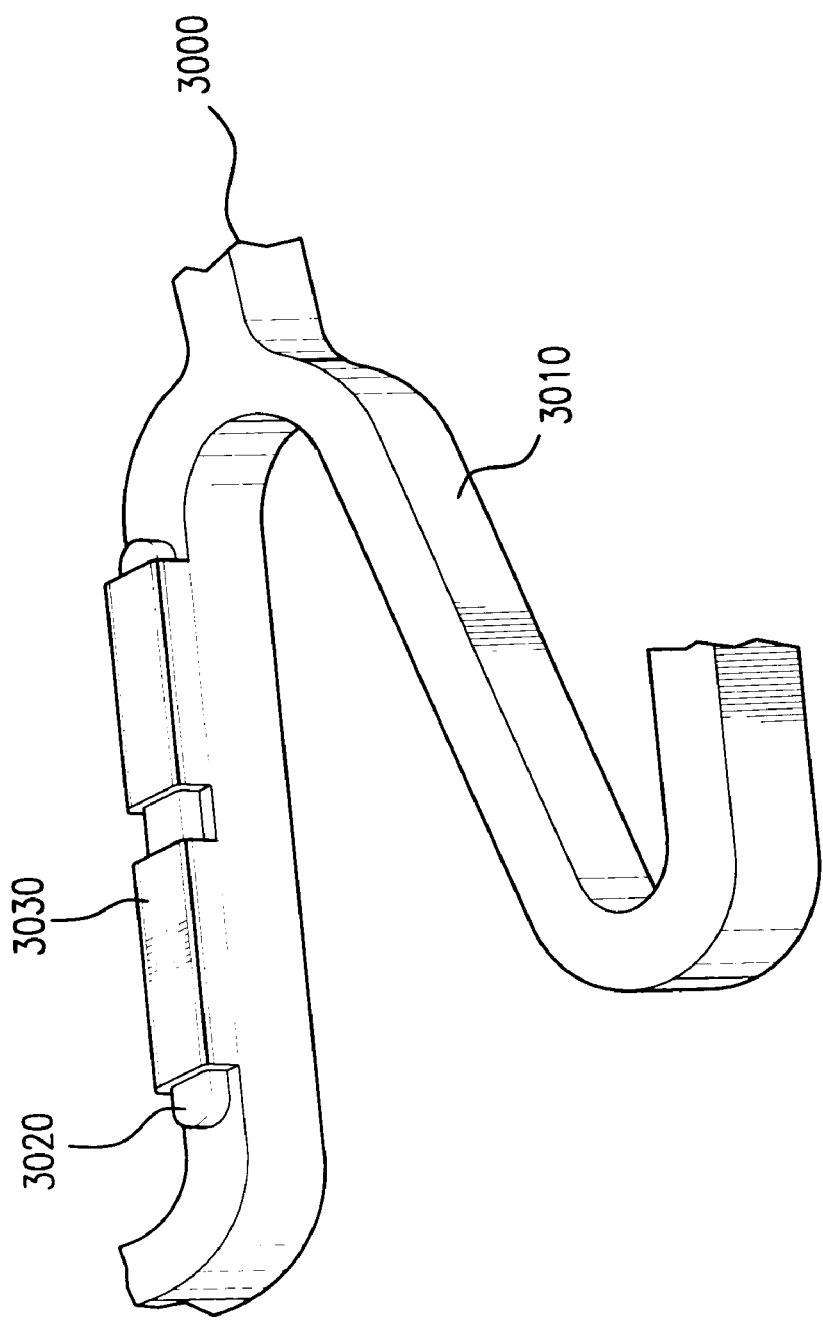
FIG. 3 is an enlarged view of still another embodiment of the invention.

FIG. 3 is an enlarged view of still another embodiment of the invention. Referring to stent 3000 of FIG. 3, segment 3010 has been coated with DNA/therapeutic agent 3020 and is shown to cover a portion of segment 3010. In other embodiments, therapeutic segment 3020 and/or barrier layer 3030 can be extended to cover the entire segment 3010 of the stent 3000 or the whole stent. In the embodiment of FIG. 3, a delicate coating material of DNA/therapeutic agent 3020 can be deposited on the surface of the stent. Thereafter, barrier layer 3030 can be deposited over portions of therapeutic agent 3020. The barrier may be bio-stable or biodegradable. If barrier layer 3030 is biodegradable, the medical device can act as a tent structure, releasing therapeutic agent 3020 over time. On the other hand, as in one embodiment of the invention, barrier layer 3030 can be designed to coat the entire length of therapeutic segment 3020. In this embodiment barrier layer 3030 can be devised as a microarray coating having varying thickness throughout the length of the covered segment.

In a further embodiment of the invention, the release profile can be controlled by varying not only the thickness of the barrier layer, but also by arranging the alternative microarray layers of therapeutic agents and barrier layers. It will be understood by an ordinary skilled artisan that various permutations of this principle, though not enumerated here, are well within the scope of this invention.

In yet another embodiment of the invention, the delivery device can be provided with different types of therapeutic agents. One or more of the therapeutic agents can have an immediate release thereby decomposing into the body faster; while one or more agent can have a sustained release dissolving into the body at a slower rate. In such embodiments, the barrier layer can have a constant or a varying thickness. Moreover, the combination of barrier layer thickness and therapeutic agent's release rate can be used to devise a desired release rate.

In yet another embodiment of the invention, the barrier layer can maintain a constant thickness over the therapeutic agents, but have different layer composition. In other words, the barrier layer can have different composition at different therapeutic sites. By supplying barrier layers of different compositions, the release rate can be controlled such that some barrier layer would absorb or degrade into the body faster than others thereby providing a faster delivery of the therapeutic agent. In contrast, one or more barrier layers can be a composite of one or more layers which, in total, release at a slower rate to provide a different drug delivery profile.

Figure 4:
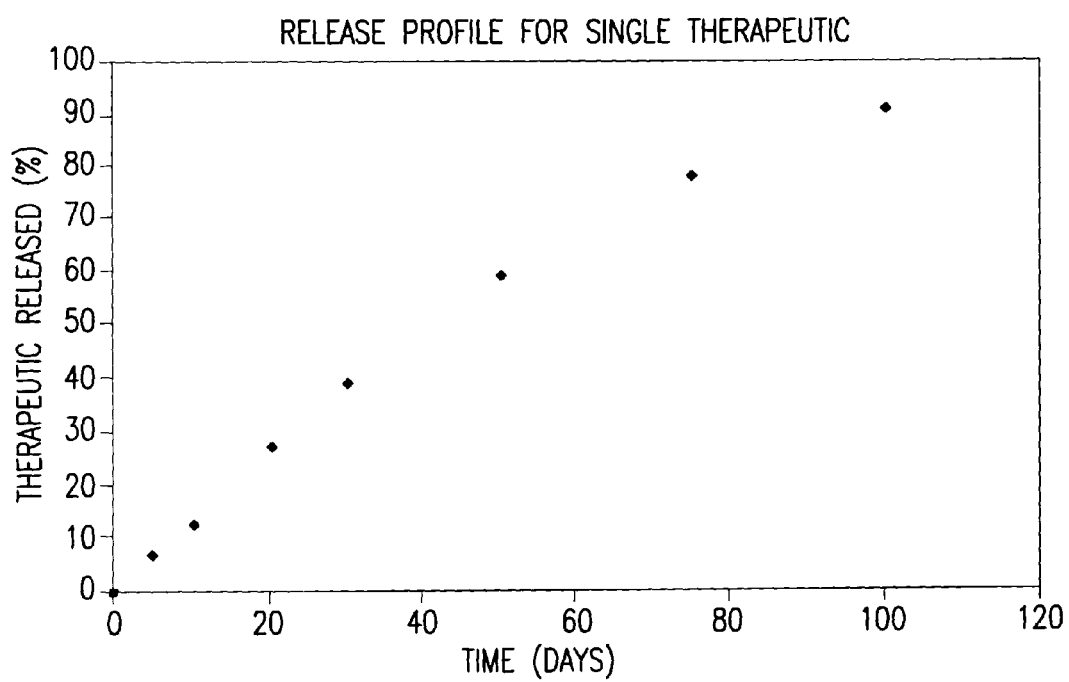
FIG. 4 is a release profile for a single therapeutic.
Figure 5:
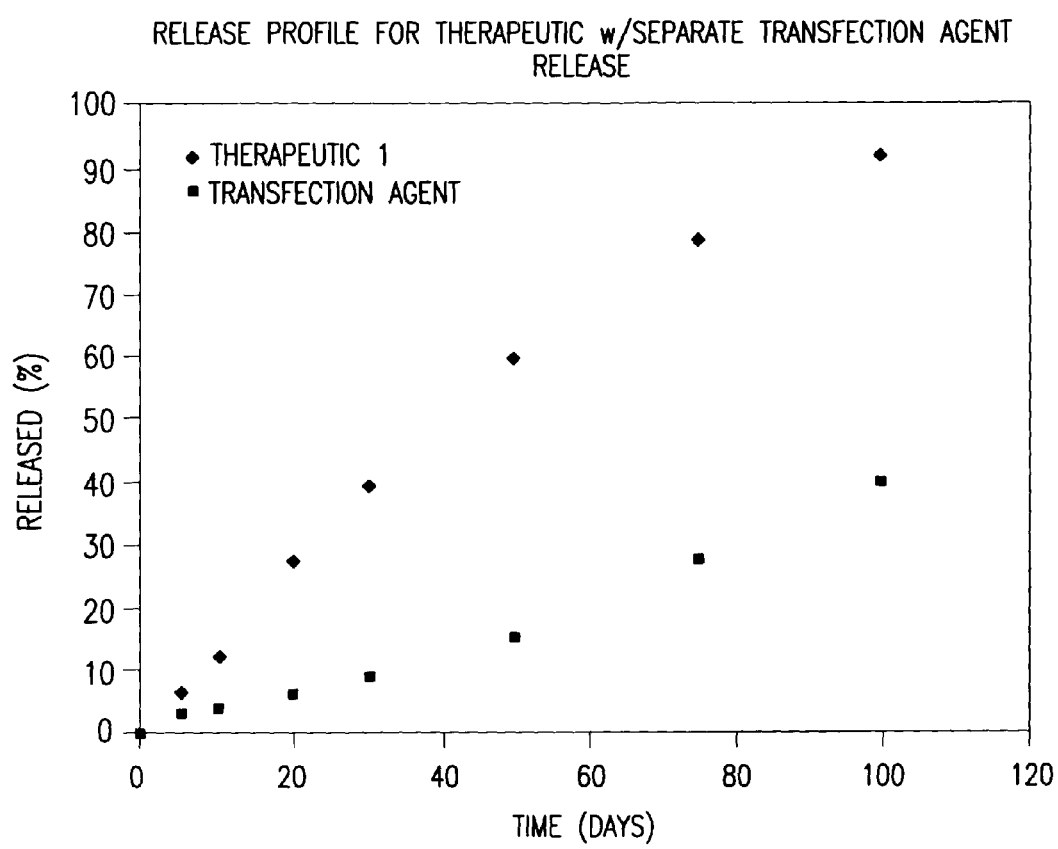
FIG. 5 is a release profile according to one embodiment of the invention where a therapeutic agent with a separate transfection agent were applied.

FIG. 4 is a release profile for a single therapeutic. Referring to FIG. 4, it can be seen that the single therapeutic agent is released in a continuous manner, though not at completely constant rate. On the other hand, FIG. 5 is a release profile according to one embodiment of the invention where a therapeutic agent with a separate transfection agent were applied. It can be seen from FIG. 5 that therapeutic agent 1 was released along with the transfection agent at different release rates.

In a method according to one embodiment of the invention, the biocompatible substrate, for example a stent or other prosthesis, is prepared by depositing one or more therapeutic agents at a plurality of sites on a substrate. Depending on the nature of the implantation and the application, the substrate can be pre-treated prior to depositing the therapeutic agent. A partial coating of suitable barrier material can be applied to each of the sites. The barrier layer can be applied to therapeutic sites as microarrays having a predefined thicknesses. By controlling the thickness and the arrangement of the microarray, the release kinetics of the therapeutic agent can be controlled.

For example, the barrier layer can be deposited to form a multi-layer coating over the therapeutic site. In this embodiment, certain therapeutic sites can have a thicker coating to ensure a slower release as compared with the sites having a relatively thinner coating. Moreover, depending on the desired release profile, microarrays forming a barrier layer can have different composition. Thus, certain barrier layers can dissolve or degrade faster than other barrier layer thereby uncovering the underlying therapeutic agent in a shorter time frame. Finally, in one embodiment of the invention, one or more biodegradable or dissolvable layer(s) can cover the entire device to enhance bio-compatibiliity or performance by, for example, making the surface more lubricated or by providing a heparin coating.

The coatings (both the therapeutic agent and the barrier material) may be applied according to conventional precision coating methods. For example, the coating may be applied by dipping or spraying using evaporative solvent materials of relatively high vapor pressure to produce the desired viscosity and the desired coating thickness. The coatings can also be applied by vapor deposition and electro deposition as are conventionally known. In one embodiment, the coating of the multi-array micro structure can be accomplished by rotating the extended stent radially while spray coating the stent with an air brush device. In this manner the coating process enables the material to adhere and conform to the shape of the stent while preserving the open lattice structure of the device.

Additionally, the coating (the therapeutic agent and/or the barrier material) may be applied using techniques described in U.S. patent application Ser. No. 09/895,415, filed Jul. 2, 2001, entitled "Coating a Medical Appliance with a Bubble Jet Printing head"; U.S. patent application Ser. No. 10/045,492, filed Jan. 14, 2002, entitled "Coating Dispensing System and Method Using a Solenoid Head for Coating Medical Devices"; and [Applicants Disclosure No. 01-D1175] entitled "Positive Displacement Coating Deposition Apparatus and Method." The disclosures of these applications are hereby incorporated by reference.

It will be recognized by one of ordinary skill in the art that the embodiments and examples described and illustrated herein are merely illustrative, as numerous other embodiments, or permutations thereof, may be implemented without departing from the spirit and scope of the present invention.

What is claimed is:

1. A method for preparing a bio-compatible stent having an extended release profile, the method comprising:
   providing a stent adapted for insertion into a body, the stent having an open lattice structure comprising a plurality of segments with open areas between the segments;
   depositing a therapeutic agent on the stent; and
   coating, at least partially, the therapeutic agent at a first site on the stent with a first barrier layer and coating, at least partially, the same therapeutic agent at a second site on the stent with a second barrier layer, wherein the second barrier layer has at least one of a different thickness or a different composition than the first barrier layer, such that the therapeutic agent at the second site has a different release rate than the therapeutic agent at the first site,
   wherein the first site and the second site are at different portions of the stent;
   wherein the first and second barrier layers are applied by a coating process such that the first and second barrier layers are adhered over the segments and do not cover open areas between the segments to preserve the open lattice structure of the stent.

2. The method of claim 1, wherein at least one of the first or the second barrier layer comprises alternating layers of a first and a second material.

3. The method of claim 1, wherein the first site and the second site are discontiguous.

4. The method of claim 1, wherein at least one of the first or the second barrier layer is a microarray of at least two sublayers.

5. The method of claim 4, wherein each of the at least two sublayers defines a different in vivo decomposition or bioabsorption rate.

6. The method of claim 4, wherein each of the at least two sublayers has a varying thickness.

7. The method of claim 1, wherein a window is interposed between the first site and the second site.

8. The method of claim 7, wherein the window exposes therapeutic agent to the body.

9. The method of claim 1, wherein at least one of the first or the second barrier layer is a microarray of materials adapted to dissolve or degrade in a body.

10. A method for preparing a bio-compatible medical device having an extended release profile, the method comprising:
    providing a medical device adapted for insertion into a body, the medical device having an open lattice structure comprising a plurality of segments with open areas between the segments;
    depositing a therapeutic agent on the medical device; and
    coating, at least partially, the therapeutic agent at a first site on the medical device with a first barrier layer and coating, at least partially, the same therapeutic agent at a second site on the medical device with a second barrier layer, wherein the second barrier layer has at least one of a different thickness or a different composition than the first barrier layer, such that the therapeutic agent at the second site has a different release rate than the therapeutic agent at the first site,
    wherein the first site and the second site are at different portions of the medical device;
    wherein the first and second barrier layers are applied by a coating process such that the first and second barrier layers are adhered over the segments and do not cover open areas between the segments to preserve the open lattice structure of the medical device.

11. The method of claim 10, wherein the first site and the second site are discontiguous.

12. The method of claim 10, wherein a window is interposed between the first site and the second site.

13. The method of claim 12, wherein the window exposes therapeutic agent to the body.

14. The method of claim 10, wherein at least one of the first or the second barrier layer is a microarray of materials adapted to dissolve or degrade in a body.

15. A bio-compatible medical device having an extended release profile, the medical device comprising:
    a substrate having an open lattice structure comprising a plurality of segments with open areas between the segments;
    a therapeutic agent deposited on the substrate; and
    a first barrier layer that coats, at least partially, the therapeutic agent at a first site on the substrate and a second barrier layer that coats, at least partially, the same therapeutic agent at a second site on the substrate, wherein the second barrier layer has at least one of a different thickness or a different composition than the first barrier layer, such that the therapeutic agent at the second site has a different release rate than the therapeutic agent at the first site, wherein the first site and the second site are at different portions of the substrate;

wherein the first and second barrier layers are adhered over the segments and do not cover open areas between the segments.

16. The medical device of claim 15, wherein the first site and the second site are discontiguous.

17. The medical device of claim 15, wherein a window is interposed between the first site and the second site.

18. The medical device of claim 17, wherein the window exposes therapeutic agent to the body.

19. The medical device of claim 15, wherein at least one of the first or the second barrier layer is a microarray of materials adapted to dissolve or degrade in a body.

20. The medical device of claim 15, wherein the medical device is a stent.

* * * * *